(12) United States Patent
Hunter

(10) Patent No.: US 9,125,838 B2
(45) Date of Patent: Sep. 8, 2015

(54) WHIPPED COMPOSITION FOR THE TREATMENT OF KERATIN FIBERS

(75) Inventor: Nikisha Hunter, Chicago, IL (US)

(73) Assignee: L'ORÉAL (FR)

( * ) Notice: Subject to any disclaimer, the term of this patent is extended or adjusted under 35 U.S.C. 154(b) by 832 days.

(21) Appl. No.: 12/722,629

(22) Filed: Mar. 12, 2010

(65) Prior Publication Data

US 2011/0224309 A1  Sep. 15, 2011

(51) Int. Cl.

| | |
|---|---|
| *A61K 8/73* | (2006.01) |
| *A61K 8/81* | (2006.01) |
| *A61K 8/84* | (2006.01) |
| *A61Q 5/00* | (2006.01) |
| *A61K 8/04* | (2006.01) |
| *A61K 8/39* | (2006.01) |
| *A61Q 5/06* | (2006.01) |

(52) U.S. Cl.
CPC . *A61K 8/73* (2013.01); *A61K 8/042* (2013.01); *A61K 8/39* (2013.01); *A61K 8/8158* (2013.01); *A61Q 5/00* (2013.01); *A61K 2800/5922* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 4,639,367 A | 1/1987 | Mackles | |
| 5,635,469 A | 6/1997 | Fowler et al. | |
| 5,965,502 A | 10/1999 | Balzer | |
| 6,251,954 B1 | 6/2001 | Roulier et al. | |
| 6,465,402 B1 * | 10/2002 | Lorant | 510/136 |
| 6,831,107 B2 * | 12/2004 | Dederen et al. | 514/777 |
| 2003/0072779 A1 * | 4/2003 | Sato et al. | 424/401 |
| 2005/0002884 A1 | 1/2005 | Jefferson | |
| 2006/0171971 A1 * | 8/2006 | Marsh et al. | 424/401 |
| 2008/0039424 A1 * | 2/2008 | Restle et al. | 514/54 |
| 2008/0152610 A1 | 6/2008 | Cajan et al. | |
| 2009/0297465 A1 | 12/2009 | Bui et al. | |

FOREIGN PATENT DOCUMENTS

| | | |
|---|---|---|
| EP | 1046387 | 2/2002 |
| EP | 1925282 | 5/2008 |
| EP | 1792600 | 1/2009 |

OTHER PUBLICATIONS

Tadros, Advances in Colloid and Interface Science, 108-109, 2004.*
CFTA International Cosmetic Ingredient Dictionary, Fourth Edition, 1991, The Cosmetic, Toiletry, and Fragrance Association, 1101 17th Street, N.W. Suite 300, Washington, DC, 20036.

* cited by examiner

*Primary Examiner* — Susan Tran
*Assistant Examiner* — William Craigo
(74) *Attorney, Agent, or Firm* — Lerner, David, Littenberg, Krumholz & Mentlik, LLP

(57) ABSTRACT

A method for treating a keratinous substrate comprising contacting the keratinous substrate with a composition containing at least one emulsifying agent comprising at least two different polysaccharides and at least one nonionic surfactant; at least one gelling agent; optionally, at least one film former, and a cosmetically acceptable carrier; wherein the composition exhibits an enhanced elastic property and the composition possesses a whipped texture.

13 Claims, 1 Drawing Sheet

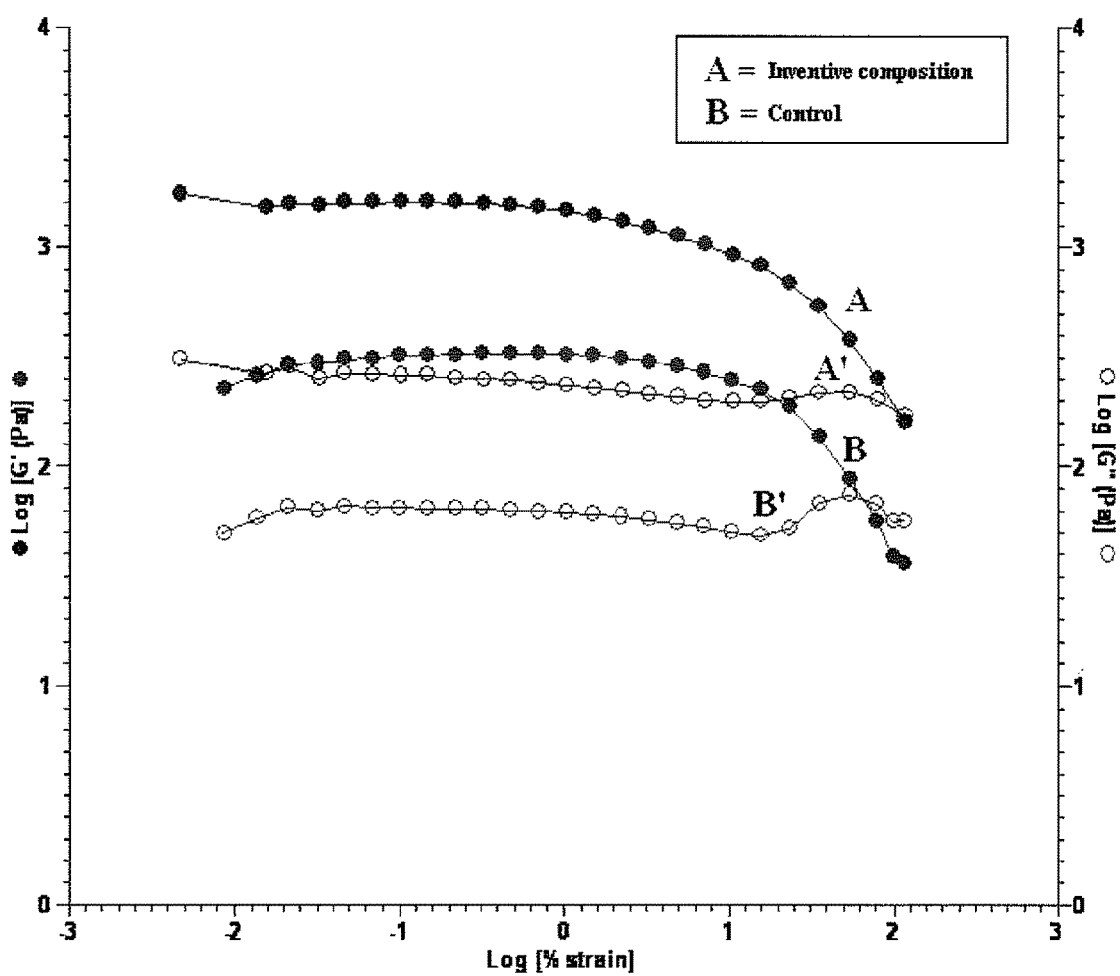

WHIPPED COMPOSITION FOR THE TREATMENT OF KERATIN FIBERS

BACKGROUND OF THE INVENTION

Consumers of cosmetic products actively seek out multi-functional, new products which are pleasing to the senses, both on application and in use, and which have innovative, interesting and/or pleasing textures, preferably without any sacrifice to functional performance. One important functional element of such compositions is their ability to condition and style the hair without weighing it down. Many consumers seek hair care products which provide a light feel, are easy to apply, moisturize, and add shine to the hair. The resulting feel and texture of the product during the application process, in addition to the feel of the hair after the application are also important elements of such commodities. While different technologies and products exist that have similar qualities, there is still a need for improvement in these areas.

Traditional hair treatment compositions on the cosmetic market appear in various forms. They can range anywhere from solutions, foams, gels, creams, waxes, serums, to aerosols and can impart a variety of levels of conditioning depending on the state of the hair. However, these conventional cosmetic compositions contain emulsifying systems which have limitations and thus are less appealing to the consumer. Such limitations may include sticky or greasy products, irritation on the scalp, a heavy or oily feel to the hair, and the use of high levels of raw materials or additional ingredients to achieve certain attributes, leading to a costly product. Furthermore, some of these traditional hair treatment products require the use of propellants in order to achieve impart certain desirable textures to the product. Therefore, there is still a need to improve currently marketed commodities in order to provide the consumer with innovative formulations that present both sensory and functionality perspectives on hair treatment products.

Thus, the object of this invention is related to a composition and process of treating the hair utilizing hair compositions with unique emulsifying systems and a whipped texture that will penetrate the hair to add moisture, but will not result in any product build up or leave the hair feeling greasy. The unique whipped texture of the cosmetic composition of the present invention may be characterized by an enhanced elastic property, a desirable bouncy texture, and significantly improved viscosity over traditional hair treatment products.

BRIEF SUMMARY OF THE INVENTION

It has surprisingly been found that hair treatment compositions having a whipped texture may be formulated using an emulsifying system comprising at least two different polysaccharides and at least one nonionic surfactant in combination with a gelling agent and a cosmetically acceptable carrier. The hair treatment composition may optionally contain a film-former. The whipped texture or consistency of such hair treatment compositions may be characterized by particular rheological parameters.

Thus, the present invention is directed to a composition for treating a keratinous material containing:
(a) at least one emulsifying agent comprising at least two different polysaccharides and at least one nonionic surfactant;
(b) at least one gelling agent;
(c) optionally, at least one film-former; and
(d) a cosmetically acceptable carrier.

The composition of the present invention exhibits an enhanced elastic property and possesses a whipped texture.

The present invention is also directed to a method for cosmetically treating a keratinous substrate comprising contacting the keratinous substrate with a composition containing:
(a) at least one emulsifying agent comprising at least two different polysaccharides and at least one nonionic surfactant;
(b) at least one gelling agent;
(c) optionally, at least one film-former; and
(d) a cosmetically acceptable carrier.

The composition of the method of the present invention exhibits an enhanced elastic property and possesses a whipped texture.

DETAILED DESCRIPTION

Other than in the operating examples, or where otherwise indicated, all numbers expressing quantities of ingredients and/or ratios of ingredients are to be understood as being modified in all instances by the term "about".

The terms "conditioning" and "condition" as used herein means imparting to at least one keratinous fiber at least one property chosen from combability, manageability, moisture-retentivity, luster, shine, smoothness and softness.

The term "pick-up" as used herein means having enough of the desired amount of the composition on an applicator or on one's finger when the applicator or finger is dipped into the composition.

As used herein, the term "rheology" means the viscosity or flow properties of the composition such that, once the composition is applied onto keratin fibers, the composition does not run or drip, and remains substantially localized at the point of application.

The term "emulsifying agent" as used herein refers to an emulsifier system that is comprised of compounds or ingredients that form an emulsion and/or aid in the formation of an emulsion.

The term "gelling agent" as used herein refers to a compound or gellifying system that is comprised of at least one compound or ingredient that modifies the rheology of the medium or composition into which it is incorporated.

The term "film-former" or "film forming agent" or "film forming resin" as used herein refers to a polymer which is capable, by itself, or in the presence of an auxiliary film-forming agent, of forming a film on a support, in particular on keratin materials.

The cosmetic compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to keratinous materials.

According to one embodiment of the present invention, there is provided a method for treating a keratinous material such as hair involving the steps of providing a hair composition containing at least one emulsifying agent comprising at least two different polysaccharides and at least one nonionic surfactant, at least one gelling agent comprising a polyacrylamide-based polymer, optionally, at least one film former, and a cosmetically acceptable carrier, and applying said composition onto the keratinous material, wherein the wherein the composition exhibits an enhanced elastic property and possesses a whipped texture.

The present invention also relates to compositions for application onto hair and which may be utilized in leave-on conditioners, hair styling products, permanent waving compositions, hair coloring products, hair care products, hair treatment and hair masque products. The present invention may also be utilized in other personal care compositions such as body washes, skin care, sun care, lip care, nail care and facial care. In addition, the inventive compositions may be used in make up products such as foundation, eye color, lip color and lip gloss.

It is to be understood that both the foregoing general description and the following detailed description are exemplary and explanatory only, and are not restrictive of the invention.

Emulsifying Agent

The emulsifying agent of the present invention comprises at least two different polysaccharides and at least one nonionic surfactant. The at least two different polysaccharides may be chosen from xanthan gum, alginates, carboxymethyl cellulose, mannans such as guar gum, locust bean gum and konjac mannan, amylase, amylopectin, glycogen, dextrans, xylans, lignins, arabans, galactans, galacturonans, chitin, chitosans, glucoronoxylans, arabinoxylans, xyloglucans, glucomannans, pectic acids and pectins, alginic acid and alginates, arabinogalactans, carrageenins, agars, glycosaminoglucans, gums Arabic, gums tragacanth, ghatti gums, karaya gums, galactomannans, cellulose and their derivatives, hydroxypropylcellulose, hydroxyethylcellulose, glucans, starches, and modified starches.

Preferably, one of the at least two different polysaccharides is xanthan gum. Also, preferably, one of the at least two different polysaccharides is a mannan. Even more preferably, the at least two different polysaccharides in the composition of the present invention are xanthan gum and a mannan.

The at least one nonionic surfactant may be of any type, such as polyoxyethylene alkyl ethers, alkoxylated fatty alcohols, polyoxyethylene sorbitan fatty acid esters, glyceryl esters and glyceryl fatty esters.

The emulsifying agents of the present invention may also comprise additional ingredients such as sucrose, esters, non-ionic surfactants, preservatives, and mixtures thereof.

Preferred emulsifying agents of the present invention include those marketed by Croda under the trade names Arlatone V-100, Arlatone V-150, and Arlatone V-175. Arlatone V-100 comprises steareth-100, steareth-2, glyceryl stearate citrate, sucrose, mannan and xanthan gum. Arlatone V-150 comprises Steareth-100, steareth-2, sucrose, mannan and xanthan gum. Arlatone V-175 comprises sucrose palmitate, glyceryl stearate, glyceryl stearate citrate, sucrose, mannan, and xanthan Gum.

The at least two different polysaccharides of the present invention are each present in an amount ranging from about 0.1% to about 1.0% by weight based on the total weight of the emulsifying agent.

The at least one nonionic surfactant of the present invention are present in an amount ranging from about 1.0% to about 10% by weight based on the total weight of the emulsifying agent.

The emulsifying agent of the present invention is present in the composition in an amount ranging from about 0.1% to about 2% weight based on the total weight of the composition, preferably ranging from about 0.3% to about 1.5% by weight based on the total weight of the composition, more preferably ranging from about 0.5% to about 1% by weight based on the total weight of the composition.

Gelling Agent

The gelling agent of the present invention may comprise polyacrylamides which may have a weight average molecular weight greater that about 50,000, preferably greater than about 100,000, to as high as 3,000,000. Additionally, the polyacrylamide polymer can, aside from being polyacrylamide itself, be a derivative thereof, and can be a mixture of a plurality of types of polymers, and can also be a copolymer with acrylamide and its derivatives as monomers.

Other gelling agents include cellulosic thickeners, such as hydroxyethylcellulose, hydroxypropylcellulose, and carboxymethylcellulose, guar gum and its derivatives, such as hydroxypropylguar, gums of microbial origin, such as xanthan gum and scleroglucan gum, and synthetic thickeners such as crosslinked homopolymers of acrylic acid and of acrylamidopropanesulphonic acid.

Other examples of gelling agents are carbomers which are high molecular weight polymers based on acrylic acid crosslinked with allyl sucrose. Variations of such copolymers are also termed carbomers. The carbomers are very effective suspending agents and have extremely high molecular weights ranging from about 700,000 to about 5,000,000. They are commercially available under the tradename Carbopol as sold by B.F. Goodrich Specialty Chemicals as water soluble acrylic acid polymers examples of which are Carbopol 910, 941, 934, 924P and 940.

The gelling agent of the present invention may further comprise other compounds to improve the gellifying and thickening properties of the gelling agent.

Thus, the gelling agent of the present invention preferably comprises at least one polyacrylamide, at least one nonionic surfactant and at least one hydrocarbon.

Representative gelling agents that employ polyacrylamide include those marketed by Seppic under the trade names Sepigel 305, Sepigel 501, Sepigel 600. Sepigel 305 is a mixture containing approximately 40% polyacrylamide, approximately 24% C13-C14 isoparaffin and approximately 6% Laureth-7 (here, Laureth-7 is a non-ionic surfactant having the formula C12H25-(OCH2CH2)n-OH, wherein n has an average value of 7). Sepigel 600 is a mixture of a acrylamide/acrylamide-2-propane sulfonate copolymer, isohexadecane and polysorbate 80 (polyoxyethylene sorbitan mono-oleate (20 EO)).

The preferred gelling agent of the present invention is Sepigel 305.

The at least one polyacrylamide may be present in an amount generally ranging from about 0.1% to about 1.0% by weight with respect to the entire weight of the gelling agent.

The at least one nonionic surfactant in the gelling agent may be of any type, such as polyoxyethylene alkyl ethers, alkoxylated fatty alcohols, polyoxyethylene sorbitan fatty acid esters, glyceryl esters and glyceryl fatty esters. The content of the non-ionic surfactant should generally range from about 0.1% to about 5.0% by weight of the gelling agent.

Examples of the at least one hydrocarbon that may be used in the gelling agent are isoparaffin, petrolatum, ceresin and squalane, with C4-C20 isoparaffins being especially suitable for use. The content of the hydrocarbon should generally range from about 0.1% to about 1.0% by weight of the gelling agent.

The at least one gelling agent of the present invention can be present in the composition in an amount generally ranging from about 0.1% to about 10% by weight based on the total weight of the composition, preferably ranging from about 0.1% to about 5% by weight based on the total weight of the composition, more preferably ranging from about 0.5% to about 1% by weight based on the total weight of the composition.

One preferred embodiment of the hair composition of the present invention does not contain nonionic surfactants other than the nonionic surfactants that are present in the at least one emulsifying agent and/or in the at least one gelling agent.

Furthermore, according to the present invention, the weight of the at least one emulsifying agent to the weight of the at least one gelling agent is in a ratio ranging from about 0.5:1 to about 4:1, preferably in a ratio ranging from about 0.75:1 to about 3:1, and more preferably in a ratio ranging from about 1:1 to about 2:1.

In other embodiments of the present invention, the weight of the at least one emulsifying agent to the weight of the at least one gelling agent is in a ratio of about 4:1, preferably, in a ratio of about 3:1, more preferably, in a ratio of about 2:1, even more preferably, in a ratio of about 1.5:1, most preferably, in a ratio of about 1:1.

Film Former

The film former which may be used in accordance with the present invention can be chosen from anionic, amphoteric and non-ionic film formers as described below.

The anionic fixing polymers generally used are polymers comprising groups derived from carboxylic, sulphonic, or phosphoric acid and have molecular weights ranging from approximately 500 to 5,000,000.

1) The carboxyl groups are contributed by unsaturated carboxylic mono- or diacid monomers such as those corresponding to the formula:

(I)

in which n is an integer from 0 to 10; A1 denotes a methylene group and when n is greater than 1, each A1 is represented by -LCH2-, where L is a heteroatom, such as oxygen or sulphur; R7 is a radical chosen from a hydrogen atom, a phenyl group, and a benzyl group; R8 is a radical chosen from a hydrogen atom, a lower alkyl group, and a carboxyl group; and R9 is a radical chosen from a hydrogen atom, a lower alkyl group, a —CH2-COOH, a phenyl group, and a benzyl group.

In the abovementioned formula, a lower alkyl radical preferably denotes a group having 1 to 4 carbon atoms and in particular methyl and ethyl.

The preferred anionic fixing polymers comprising carboxyl groups according to the invention are:

(A) Homo- or copolymers of acrylic or methacrylic acid or their salts and in particular the products sold under the names Versicol E or K by the company Allied Colloid and Ultrahold by the company BASF. The copolymers of acrylic acid and of acrylamide sold in the form of their sodium salt under the names Reten 421, 423, or 425 by the company Hercules or the sodium salts of polyhydroxycarboxylic acids.

(B) Copolymers of acrylic acid or methacrylic acid with a monoethylenic monomer, such as ethylene, styrene, vinyl esters, or esters of acrylic or methacrylic acid, optionally grafted onto a polyalkylene glycol, such as polyethylene glycol, and optionally crosslinked. The copolymers of this type comprising, in their chain, an optionally N-alkylated and/or -hydroxyalkylated acrylamide unit or provided under the name Quadramer by the company American Cyanamid. Mention may also be made of copolymers of acrylic acid and of C1-C4 alkyl methacrylate and terpolymers of vinylpyrrolidone, of acrylic acid, and of C1-C20 alkyl methacrylate for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

(C) copolymers derived from crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbon chain, such as those comprising at least 5 carbon atoms, it optionally being possible for these polymers to be grafted and crosslinked, or alternatively a vinyl, allyl, or methallyl ester of an alpha- or beta-cyclic carboxylic acid. Commercial products coming within this class are the Resins 28-29-30, 26-13-14 and 28-13-10 sold by the company National Starch.

(D) copolymers derived from C4-C8 monounsaturated carboxylic acids or anhydrides chosen from:

copolymers comprising (i) one or more maleic, fumaric, or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated; and in particular those sold under the names Gantrez AN or ES by the company ISP.

copolymers comprising (i) one or more maleic, citraconic, or itaconic anhydrides and (ii) one or more monomers chosen from allyl or methallyl esters, optionally comprising one or more acrylamide, methacrylamide, alpha-olefin, acrylic or methacrylic ester, acrylic or methacrylic acid, or vinylpyrrolidone groups in their chain.

The anhydride functional groups of these copolymers optionally being monoesterified or monoamidated.

(E) polyacrylamides comprising carboxylate groups.

2) The polymers comprising sulpho groups are polymers comprising vinylsulphonic, styrenesulphonic, naphthalenesulphonic, or acrylamidoalkylsulphonic units derived from sulfonic acid.

These polymers can in particular be chosen from:

salts of polyvinylsulphonic acid having a molecular weight that ranges from approximately 1000 to 100,000, as well as copolymers with an unsaturated comonomer, such as acrylic or methacrylic acids and their esters as well as acrylamide or its derivatives, vinyl ethers, and vinylpyrrolidone.

salts of polystyrenesulphonic acid, the sodium salts having a molecular weight of approximately 500,000 and of approximately 100,000 sold respectively under the names Flexan 500 and Flexan 130 by National Starch.

salts of polyacrylamidesulphonic acids, and more particularly the polyacrylamidoethylpropanesulphonic acid sold under the name Cosmedia Polymer HSP 1180 by Henkel.

According to the invention, the anionic fixing polymers are preferably chosen from acrylic acid copolymers, such as the acrylic acid/ethyl acrylate/N-tert-butylacrylamide terpolymer sold under the name Ultrahold Strong by the company BASF; copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; polymers derived from maleic, fumaric, or itaconic acids or anhydrides with vinyl esters, vinyl ethers, vinyl halides, phenylvinyl derivatives, or acrylic acid and its esters, such as the monoesterified methyl vinyl ether/maleic anhydride copolymer sold under the name Gantrez ES 425 by the company ISP; copolymers of methacrylic acid and of methyl methacrylate sold under the name Eudragit L by the company Rohm Pharma; the copolymer of methacrylic acid and of ethyl acrylate sold under the name Luvimer MAEX or MAE by the company BASF; the vinyl acetate/crotonic acid copolymer sold under the name Luviset CA 66 by the company BASF; and the vinyl acetate/crotonic acid copolymer grafted by polyethylene glycol sold under the name Aristoflex A by the company BASF.

The most particularly preferred anionic fixing polymers are chosen from the monoesterified methyl vinyl ether/maleic anhydride copolymer sold under the name Gantrez ES 425 by the company ISP; the acrylic acid/ethyl acrylate/N-tert-butylacrylamide terpolymer sold under the name Ultrahold Strong by the company BASF; the copolymers of methacrylic acid and of methyl methacrylate sold under the name Eudragit L by the company Rohm Pharma; the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; the copolymer of methacrylic acid and of ethyl acrylate sold under the name Luvimer MAEX or MAE by the company BASF; and the vinylpyrrolidone/acrylic acid/lauryl methacrylate terpolymer sold under the name Acrylidone LM by the company ISP.

The amphoteric fixing polymers which can be used in accordance with the invention can be chosen from polymers comprising X and Y units distributed randomly in the polymer chain, where X denotes a unit derived from a monomer comprising at least one basic nitrogen atom and Y denotes a unit derived from an acidic monomer comprising one or more carboxyl or sulpho groups or else X and Y can denote groups derived from zwitterionic carboxybetaine or sulphobetaine monomers; X and Y can also denote a cationic polymer chain comprising primary, secondary, tertiary, or quaternary amine groups, in which at least one of the amine groups carries a carboxyl or sulpho group connected via a hydrocarbon radical, or else X and Y form part of a chain of a polymer comprising an alpha, beta-dicarboxyethylene unit, one of the carboxyl groups of which has been reacted with a polyamine comprising one or more primary or secondary amine groups.

The most particularly preferred amphoteric fixing polymers corresponding to the definition given above are chosen from the following polymers:

(1) polymers resulting from the copolymerization of a monomer derived from a vinyl compound carrying a carboxyl group, particularly acrylic acid, methacrylic acid, maleic acid, or alpha-chloracrylic acid, and of a basic monomer derived from a substituted vinyl compound comprising at least one basic atom, particularly dialkylaminoalkyl methacrylate and acrylate or dialkylaminoalkylmethacrylamide and -acrylamide.

(2) polymers comprising units derived:
a) from at least one monomer chosen from acrylamides or methacrylamides substituted on the nitrogen by an alkyl radical,
b) from at least one acidic comonomer comprising one or more reactive carboxyl groups, and
c) from at least one basic comonomer, such as esters comprising primary, secondary, tertiary, and quaternary amine substituents of acrylic and methacrylic acids and the quaternization product of dimethylaminoethyl methacrylate with dimethyl or diethyl sulphate.

The more particularly preferred N-substituted acrylamides or methacrylamides according to the invention are the groups in which the alkyl radicals comprise from 2 to 12 carbon atoms and more particularly N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers are more particularly chosen from acrylic, methacrylic, crotonic, itaconic, maleic, or fumaric acids and alkyl monoesters having 1 to 4 carbon atoms of maleic or fumaric acids or anhydrides. The preferred basic comonomers are aminoethyl, butylaminoethyl, N,N'-dimethylaminoethyl, or N-tert-butylaminoethyl methacrylates.

Use is particularly made of the copolymers for which the CTFA name (4th Ed., 1991) is octylacrylamide/acrylates/butylaminoethyl methacrylate copolymer, such as the products sold under the name Amphomer or Lovocryl 47 by the company National Starch.

(3) partially or completely alkylated and crosslinked polyaminoamides derived from polyamino-amides of general formula II:

$$+CO-R_{10}-CO-Z+ \qquad (II)$$

in which R10 represents a divalent radical derived from a saturated dicarboxylic acid, from an aliphatic mono- or dicarboxylic acid comprising an ethylenic double bond, from an ester of a lower alkanol having 1 to 6 carbon atom of these acids, or from a radical derived from the addition of any one of the said acids with a bisprimary or bissecondary amine; and Z denotes a radical of a bisprimary, mono- or bissecondary polyalkylenepolyamine and preferably represents:

a) in the proportions of 60 mol percent to 100 mol percent, the radical III:

$$-NH+(CH_2)_x-NH+_p \qquad (III)$$

where x=2 and p=2 or 3, or else x=3 and p=2 and where this radical derives from diethylenetriamine, triethylenetetraamine, or dipropylenetriamine;

b) in the proportions of 0 mol percent to 40 mol percent, the above radical (III), in which x=2 and p=1 and which derives from ethylenediamine, or the radical derived from piperazine:

c) in the proportions of 0 mol percent to 20 mol percent, the radical —NH—(CH2)6-NH— derived from hexamethylenediamine, these polyaminoamines being crosslinked by addition of a bifunctional crosslinking agent chosen from epihalohydrins, diepoxides, dianhydrides, or bisunsaturated derivatives, by means of 0.025 mol to 0.35 mol of crosslinking agent per amine group of the polyaminoamide, and alkylated by reaction with acrylic acid, chloracetic acid, or an alkanesultone or their salts.

The saturated carboxylic acids are preferably chosen from acids having 6 to 10 carbon atoms, such as adipic, 2,2,4-trimethyladipic and 2,4,4-trimethyladipic, or terephthalic acid, and the acids comprising an ethylenic double bond, such as, for example, acrylic, methacrylic, or itaconic acids.

The alkanesultones used in the alkylation are preferably propane- or butanesultone. The salts of the alkylating agents are preferably the sodium or potassium salts.

(4) polymers comprising zwitterionic units of formula IV:

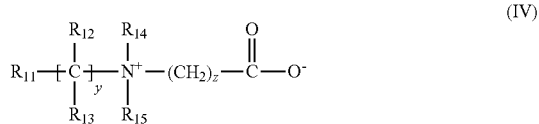

(IV)

in which R11 denotes a polymerizable unsaturated group, such as an acrylate, methacrylate, acrylamide, or methacrylamide group; y and z represents an integer from 1 to 3; R12 and R13 are radicals chosen from a hydrogen atom, methyl, ethyl, and propyl; and R14 and R15 are radicals chosen from a hydrogen atom and an alkyl radical such that the sum of the carbon atoms in R14 and R15 does not exceed 10.

The polymers comprising such units can also comprise units derived from non-zwitterionic monomers, such as dimethyl- or diethylaminoethyl acrylate or methacrylate, alkyl acrylates or methacrylates, acrylamides or methacrylamides, or vinyl acetate.

Mention may be made, by way of example, of the methyl methacrylate/methyl dimethylcarboxymethylammonioethyl methacrylate copolymer, such as the product sold under the name Diaformer Z301 by the company Sandoz.

(5) polymers derived from chitosan comprising monomer units corresponding to the following formulae:

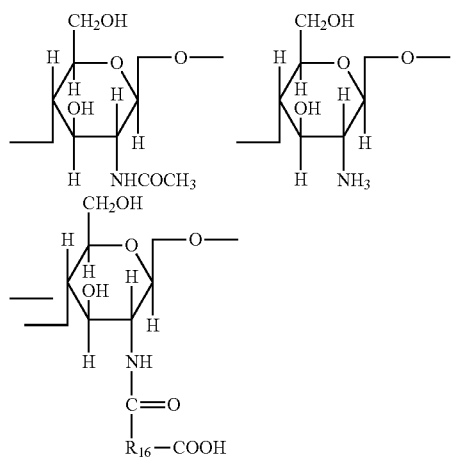

the unit D being present in proportions ranging from 0 percent to 30 percent, the unit E in proportions ranging from 5 percent to 50 percent and the unit F in proportions ranging from 30 percent to 90 percent, it being understood that, in this unit F, R16 represents a radical of formula:

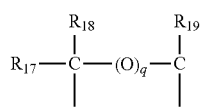

in which, if q=0, R17, R18, and R19, which are identical or different, each represent a hydrogen atom, a methyl, hydroxyl, acetoxy, or amino residue, a monoalkylamine residue or a dialkylamine residue, optionally interrupted by one or more nitrogen atoms and/or optionally substituted by one or more amine, hydroxyl, carboxy, alkylthio, or sulpho groups, or an alkylthio residue in which the alkyl group carries an amino residue, at least one of the R17, R18, and R19 radicals being, in this case, a hydrogen atom; or, if (q=1, R17, R18, and R19 each represent a hydrogen atom, and the salts formed by these compounds with bases or acids.

(6) Polymers derived from the N-carboxyalkylation of chitosan, such as the N-(carboxymethyl)chitosan or the N-(carboxybutyl)chitosan sold under the name "Evalsan" by the company Jan Dekker.

(7) Polymers corresponding to the general formula (V):

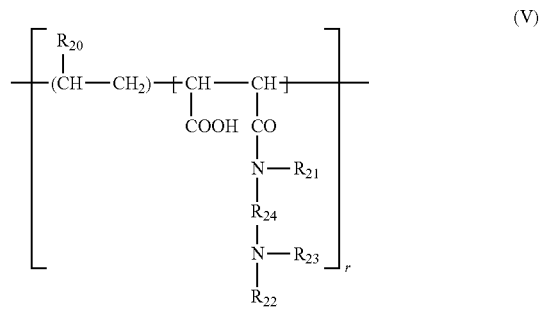

(V)

in which R20 is a radical chosen from a hydrogen atom, a CH3O, CH3CH2O, and phenyl radical; R21 denotes hydrogen or a lower alkyl radical such as methyl or ethyl; R22 denotes hydrogen or a lower alkyl radical such as methyl or ethyl; and R23 denotes a lower alkyl radical such as methyl or ethyl or a radical corresponding to the formula: —R24-N (R22)2, where R24 represents a —CH2-CH2-, —CH2-CH2-CH2-, or —CH2-CH(CH3)- group and R22 having the meanings mentioned above, and the higher homologues of these radicals comprising up to 6 carbon atoms.

(8) Amphoteric fixing polymers of the -D-X-D-X- type chosen from:

a) polymers obtained by reaction of chloracetic acid or sodium chloracetate with compounds comprising at least one unit of formula:

-D-X-D-X-D- (VI)

where D denotes a radical:

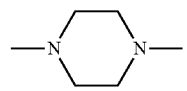

and X denotes the symbol E or E'. E and E', which are identical or different, denote a bivalent radical chosen from straight- and branched-chain alkylene radicals comprising up to 7 carbon atoms in the main chain, which is unsubstituted or substituted by hydroxyl groups and which can additionally comprise oxygen, nitrogen, or sulphur atoms or 1 to 3 aromatic and/or heterocyclic rings; the oxygen, nitrogen, and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester, and/or urethane groups.

b) Polymers of formula:

-D-X-D-X- (VI')

where D denotes a radical:

and X denotes the symbol E or E' and E' at least once, where E has the meaning indicated above and E' is a bivalent radical chosen from straight- and branched-chain alkylene radicals having up to 7 carbon atoms in the main chain, which is substituted or unsubstituted by one or more hydroxyl radicals and which comprises one or more nitrogen atoms, the nitrogen atom being substituted by an alkyl chain optionally interrupted by an oxygen atom and necessarily comprising one or more carboxyl functional groups or one or more hydroxyl functional groups and betainized by reaction with chloracetic acid or sodium chloracetate.

(9) (C1-C5)alkyl vinyl ether/maleic anhydride copolymers, which is partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

The particularly preferred amphoteric fixing polymers according to the invention are those of the family (3), such as the copolymers with the CTFA name (4Ed. 1991) of octylacrylamide/acrylates/butylaminoethyl methacrylate copolymer, such as the products sold under the names Amphomer, Amhomer LV 71, or Lovocryl 47 by the company National Starch, and those of the family (4), such as methyl methacrylate/methyl dimethylcarboxymethylammonioethyl methacrylate copolymer, for example sold under the name Diaformer Z301 by the company Sandoz.

The non-ionic fixing polymers which can be used according to the present invention are chosen, for example, from:

vinylpyrrolidone homopolymers;

copolymers of vinylpyrrolidone and of vinyl acetate;

polyalkyloxazolines, such as the polyethyloxazolines provided by the company Dow Chemical under the names PEOX 50 000, PEOX 200 000 and PEOX 500 000;

vinyl acetate homopolymers, such as the product provided under the name Appretan EM by the company Hoechst or the product provided under the name Rhodopas A 012 by the company Rhone-Poulenc;

copolymers of vinyl acetate and of acrylic ester, such as the product provided under the name Rhodopas AD 310 from Rhone-Poulenc;

copolymers of vinyl acetate and of ethylene, such as the product provided under the name Appretan TV by the company Hoechst;

copolymers of vinyl acetate and of maleic ester, for example of dibutyl maleate, such as the product provided under the name Appretan MB Extra by the company Hoechst;

copolymers of polyethylene and of maleic anhydride;

alkyl acrylate homopolymers and alkyl methacrylate homopolymers, such as the product provided under the name Micropearl RQ 750 by the company Matsumoto or the product provided under the name Luhydran A 848 S by the company BASF;

acrylic ester copolymers, such as, for example, copolymers of alkyl acrylates and of alkyl methacrylates, such as the products provided by the company Rohm and Haas under the names Primal AC-261 K and Eudragit NE 30 D, by the company BASF under the names Acronal 601, Luhydran R 8833 or 8845, or by the company Hoechst under the names Appretan N 9213 or N9212;

copolymers of acrylonitrile and of a non-ionic monomer chosen, for example, from butadiene and alkyl (meth)acrylates; mention may be made of the products provided under the names Nipol LX 531 B by the company Nippon Zeon or those provided under the name CJ 0601 B by the company Rohm and Haas;

polyurethanes, such as the products provided under the names Acrysol RM 1020 or Acrysol RM 2020 by the company Rohm and Haas or the products Uraflex XP 401 UZ or Uraflex XP 402 UZ by the company DSM Resins;

copolymers of alkyl acrylate and of urethane, such as the product 8538-33 by the company National Starch;

polyamides, such as the product Estapor LO 11 provided by the company Rhone-Poulenc; and chemically modified or unmodified non-ionic guar gums.

The unmodified non-ionic guar gums are, for example, the products sold under the name Vidogum GH 175 by the company Unipectine and under the name Jaguar C by the company Meyhall. The modified non-ionic guar gums, which can be used according to the invention, are preferably modified by C1-C6 hydroxyalkyl groups. Mention may be made, by way of example, of the hydroxymethyl, hydroxyethyl, hydroxypropyl, and hydroxybutyl groups. These guar gums are well known in the state of the art and can, for example, be prepared by reacting the corresponding alkene oxides, such as, for example, propylene oxides, with guar gum, so as to obtain a guar gum modified by hydroxypropyl groups.

Such non-ionic guar gums optionally modified by hydroxyalkyl groups are, for example, sold under the trade names Jaguar HP8, Jaguar HP60, Jaguar HP120, Jaguar DC 293, and Jaguar HP 105 by the company Meyhall or under the name Galactasol 4H4FD2 by the company Aqualon.

The alkyl radicals of the non-ionic fixing polymers have from 1 to 6 carbon atoms, unless otherwise mentioned.

The non-ionic fixing polymer which are very particularly suitable for the preparation of the compositions in accordance with the invention are those chosen from:

vinyllactam copolymers, such as copolymers of vinylpyrrolidone and of vinyl acetate and vinylpyrrolidone/vinyl acetate/vinyl propionate copolymers;

the polyvinylcaprolactam Luviskol Plus (BASF);

vinyl acetate homopolymers, such as Appretan EM (Hoechst) or Rhodopas A 012 (Rhone-Poulenc);

polyalkyloxazolines, such as PEOX 50 000 and PEOX 500 000 (Dow Chemical);

copolymers of vinyl acetate and of acrylic ester, such as Rhodopas AD 310 (Rhone-Poulenc);

copolymers of vinyl acetate and of ethylene, such as Appretan TV (Hoechst);

copolymers of vinyl acetate and of maleic ester, such as Appretan MB Extra (Hoechst);

alkyl acrylate homopolymers and alkyl metacrylate homopolymers, such as Luhydran A 848 S (BASF);

acrylic ester copolymers, such as Primal AC-261 K (Roehm and Haas), Acronal 610 (BASF) or Appretan N 9213 (Hoechst);

copolymers of acrylonitrile and of a non-ionic monomer, such as CJ 0601 B (Roehm and Haas);

polyurethanes, such as Acrysol RM 1020 or Acrysol RM 2020 (Roehm and Haas);

copolymers of alkyl acrylate and of urethane, such as 8538-33 (National Starch); and polyamides, such as Estapor LO 11 (Rhone-Poulenc).

According to the invention, it is also possible to use fixing polymers of grafted silicone type comprising a polysiloxane portion and a portion composed of a non-silicone organic chain, one of the two portions constituting the main chain of the polymer and the other being grafted onto the said main chain. These polymers are preferably anionic or non-ionic.

Such polymers are, for example, the copolymers capable of being obtained by radical polymerization from the mixture of monomers composed of:

a) 50 percent to 90 percent by weight of tert-butyl acrylate;
b) 0 percent to 40 percent by weight of acrylic acid;
c) 5 percent to 40 percent by weight of silicone macromer of formula:

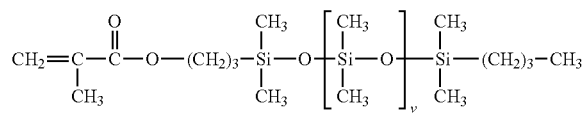

where v is a number ranging from 5 to 700; the percentages by weight being calculated with respect to the total weight of the monomers.

Other examples of grafted silicone polymers are in particular polydimethylsiloxanes (PDMS) on which are grafted, via a connecting link of thiopropylene type, mixed polymer units of the poly(meth)acrylic acid type and of the poly(alkyl (meth)acrylate) type and polydimethylsiloxanes (PDMS) on which are grafted, via a connecting link of thiopropylene type, polymer units of the poly(isobutyl (meth)acrylate) type.

Cosmetically Acceptable Carrier

The at least one solvent may be chosen from water, organic solvents and mixtures thereof. By way of organic solvent, suitable examples may be chosen from C1-C4 lower alkanols, such as ethanol and isopropanol; for example, polyols and polyol ethers such as 2-butoxyethanol, propylene glycol, propylene glycol monomethyl ether, diethylene glycol monoethyl ether and monomethyl ether, for example, and aromatic alcohols such as benzyl alcohol or phenoxyethanol, for example, and isododecane, and mixtures thereof. Other examples of solvents for use in the present invention are hexyleneglycol and dipropylene glycol, and mixtures thereof.

In one embodiment of the present invention, the solvent is water.

In another embodiment of the present invention, the composition uses an organic solvent.

In another embodiment of the present invention, the composition uses a polar organic solvent.

The composition(s) of the present invention may also comprise additives, for instance those chosen from a non-exhaustive list of reducing agents, surfactants, antioxidants, sequestering agents, softeners, antifoams, moisturizers, emollients, basifying agents, gelling agents, wetting agents, thickening agents, spreading agents, dispersants, plasticizers, preservatives, sunscreens, direct dyes or oxidation dyes, pigments, mineral fillers, clays, colloidal minerals, nacres, nacreous agents, emulsifying agents, fragrances, peptizers, preserving agents, fixing or non-fixing polymers, ceramides, proteins, active agents, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The compositions of the present invention are preferably formulated as oil-in water or water-in-oil emulsion creams or thick lotions having desirable rheological properties characterized by enhanced elastic properties and significantly improved viscosity over traditional hair treatment products.

The compositions of the present invention are also characterized by their unique whipped texture having rheological properties such as viscosity or flow properties such that, once applied onto keratinous substrates, the inventive composition does not run or drip, and remains substantially localized at the point of application.

The texture of the compositions of the present invention may also be characterized by visco-elastic measurements on a rheometer.

According to one embodiment of the present invention, there is provided a process for treating keratinous materials, such as hair or skin, by applying the above-disclosed composition onto the keratinous material. The precise amount of composition to be applied onto the material will depend on the degree of treatment desired.

The inventive composition may be prepared by dispersing the emulsifying agent in the carrier, homogenizing the resultant mixture, and then adding the gelling agent.

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, unless otherwise specified.

Example 1

Hair Treatment Composition

Hair Treatment Composition

| US INCI NAME | % |
|---|---|
| XANTHAN GUM | 0.05 |
| STEARYL ALCOHOL | 4 |
| STEARETH-2 | 0.23 |
| LAURETH-7 | 0.07 |
| MANNAN | 0.05 |
| POLYACRYLAMIDE | 0.4 |
| MYRISTIC ACID | 0.09 |
| PALMITIC ACID | 1.32 |
| STEARIC ACID | 1.59 |
| C13-14 ISOPARAFFIN | 0.21 |
| CAPRYLIC/CAPRIC TRIGLYCERIDE | 25 |
| WATER | 66.32 |
| STEARETH-100 | 0.67 |
| PRESERVATIVE | Q.S. |
| FRAGRANCE | Q.S |
| Total (including VI): | 100 |

Example 2

Hairdress

Hairdress

| US INCI NAME | % |
|---|---|
| XANTHAN GUM | 0.0375 |
| STEARYL ALCOHOL | 4 |
| STEARETH-2 | 0.1725 |
| LAURETH-7 | 0.07875 |
| MANNAN | 0.0375 |

-continued

| US INCI NAME | % |
|---|---|
| POLYACRYLAMIDE | 0.45 |
| MYRISTIC ACID | 0.09 |
| PALMITIC ACID | 1.32 |
| STEARIC ACID | 1.59 |
| C13-14 ISOPARAFFIN | 0.23625 |
| CAPRYLIC/CAPRIC TRIGLYCERIDE | 25 |
| WATER | 66.485 |
| STEARETH-100 | 0.5025 |
| PRESERVATIVE | Q.S. |
| FRAGRANCE | Q.S. |
| Total (including VI): | 100 |

Example 3

Styling Hairdress

Styling Hairdress

| US INCI NAME | % |
|---|---|
| XANTHAN GUM | 0.0375 |
| STEARYL ALCOHOL | 4 |
| STEARETH-2 | 0.1725 |
| LAURETH-7 | 0.07875 |
| MANNAN | 0.0375 |
| POLYACRYLAMIDE | 0.45 |
| MYRISTIC ACID | 0.09 |
| PALMITIC ACID | 1.32 |
| STEARIC ACID | 1.59 |
| C13-14 ISOPARAFFIN | 0.23625 |
| CAPRYLIC/CAPRIC TRIGLYCERIDE | 25 |
| WATER | 61.485 |
| STEARETH-100 | 0.5025 |
| PVP | 3.0 |
| VP/VA Copolymer | 2.0 |
| PRESERVATIVE | Q.S. |
| FRAGRANCE | Q.S. |
| Total (including VI): | 100 |

Rheology Measurements for Elastic Property

The rheology of the inventive composition was characterized by its elastic and viscous properties.

Rheology measurements of the inventive composition were conducted using a Control Stress Rheomter AR-2 from TA Instrument. The instrument contains a parallel hatched plate with a diameter of 40 mm and a gap of 1000 microns.

The experiments involved a strain sweep test at a fixed frequency of 1 rad/s, a frequency sweep test from 100 rad/s to 0.1 rad/s in the linear regime, and a temperature of 25 degrees Celsius through the experiment.

Two samples were tested and compared in terms of elastic function and viscous function. The first sample was the inventive composition containing 3% of the gelling agent Sepigel and the second sample was a control sample and did not contain the gelling agent. FIG. 1 below shows several visco-elastic curves or linear regimes which were measured using the strain sweep test. The first sample corresponds to curves A and A' below and the second sample corresponds to curves B and B'. The curves A and B with solid circles represent the elastic function of the samples tested and the curves A' and B' with the open circles represent the viscous function of the samples tested.

The FIGURE above shows that for the first sample, the inventive composition, the elastic function is above about 2.2 Pa and the viscous function is at least about 2.2 Pa at the highest % strain or stress applied to the composition. In contrast, the second sample, the control composition, exhibited elastic and viscous functions at below 2 Pa at the highest % strain applied and which did not go higher than 2.5 Pa as the amount of strain on the control composition decreased. Therefore, the first sample, the inventive composition, possessed higher elastic and viscous functions than those of the second sample (control sample). A higher visco-elastic function for the inventive composition corresponded to better cosmetic properties to the composition in terms of pick up, whipped texture, bouncy texture and rheology.

What is claimed is:

1. A cosmetic composition comprising:
   (a) at least one emulsifying agent comprising at least two different polysaccharides which are xanthan gum and a mannan, and at least two nonionic surfactants which are steareth-100 and steareth-2, wherein the agent is present in an amount ranging from about 0.1% to about 2% by weight based on the total by weight, of the composition;
   (b) at least one gelling agent comprising at least one polyacrylamide, at least one nonionic surfactant which is a polyoxyethylene alkyl ether, and at least one hydrocarbon which is a C4-C20 isoparaffin;
   (c) a cosmetically acceptable carrier; and
   (d) optionally, at least one film former;
   wherein the composition has a whipped texture.

2. The composition according to claim 1, wherein the emulsifying agent further comprises sucrose.

3. The composition according to claim 1, wherein the at least one emulsifying agent is present in an amount ranging from about 0.3% to about 1.5% by weight, based on the total weight of the composition.

4. The composition according to claim 1, wherein the at least one emulsifying agent is present in an amount ranging from about 0.5% to about 1% by weight, based on the total weight of the composition.

5. The composition according to claim 1, wherein the at least one gelling agent is present in an amount ranging from about 0.1% to about 10% by weight, based on the total weight of the composition.

6. The composition according to claim 1, wherein the at least one gelling agent is present in an amount ranging from about 0.1% to about 5% by weight, based on the total weight of the composition.

7. The composition according to claim 1, wherein the at least one gelling agent is present in an amount ranging from about 0.1% to about 1% by weight, based on the total weight of the composition.

8. The composition according to claim 1, wherein the ratio of the weight of the at least one emulsifying agent to the weight of the at least one gelling agent is 0.5:1 to 3:1.

9. The composition according to claim 1, wherein the at least one film former is chosen from anionic film formers, amphoteric film formers, nonionic film formers and mixtures thereof.

10. The composition according to claim 1, wherein the at least one film former is chosen from PVP, polyquaternium-39, VP/dimethylaminoethylmethacrylate copolymer, octylacrylamide/acrylates/butylaminoethyl methacrylate copolymer, acrylate-based film formers, and mixtures thereof.

11. A composition according to claim 1, wherein the cosmetically acceptable carrier is chosen from water, organic solvents and mixtures thereof.

12. The composition of claim 1, which exhibits an elastic function above about 2.2 Pa and a viscous function of at least about 2.2 Pa, measured in accordance with a strain sweep test at a fixed frequency of 1 rad/s, a frequency sweep test from 100 rad/s to 0.1 rad/s in the linear regime, and a temperature of 25 degrees Celsius.

13. A method for cosmetically treating a keratinous substrate comprising contacting the keratinous substrate with a composition containing:
   (a) at least one emulsifying agent comprising at least two different polysaccharides which are xanthan gum and a mannan, and at least two nonionic surfactants which are steareth-100 and steareth-2, wherein the agent is present in an amount ranging from about 0.1% to about 2% by weight based on the total by weight, of the composition;
   (b) at least one gelling agent comprising at least one polyacrylamide, at least one nonionic surfactant which is a polyoxyethylene alkyl ether, and at least one hydrocarbon which is a C4-C20 isoparaffin;
   (c) a cosmetically acceptable carrier; and
   (d) optionally, at least one film former;
wherein the composition has a whipped texture.

* * * * *